United States Patent [19]

Franz

[11] Patent Number: 4,839,347
[45] Date of Patent: Jun. 13, 1989

[54] COMPOSITION FOR TREATING DEHYDRATION
[75] Inventor: Peter H. Franz, Edina, Minn.
[73] Assignee: Techmix, Inc., Edina, Minn.
[21] Appl. No.: 675,981
[22] Filed: Nov. 29, 1984
[51] Int. Cl.$^4$ .............................................. A61K 31/70
[52] U.S. Cl. ....................................... 514/53; 514/23; 426/801; 426/806; 426/810
[58] Field of Search .................... 514/23, 53; 426/801, 426/806, 810

[56] References Cited
U.S. PATENT DOCUMENTS

| | | |
|---|---|---|
| 3,898,328 | 7/1975 | Beigler et al. |
| 3,928,574 | 4/1975 | Phillips. |
| 4,164,568 | 6/1979 | Bywater. |
| 4,322,407 | 3/1982 | Ko ......................................... 514/23 |

OTHER PUBLICATIONS

"Dietary Manipulation of Gastric pH in the Prophyl-axis of Enteric Disease in Weaned Pigs: Some Field Observations," Thomlinson, J. R. and Lawrence, T. L. J., The Veterinary Record, Aug. 8, 1981, pp. 120–122.
"Vaccines May Delay Scours; Dutch Claim Cure Discovered," National Hog Farmer, Dec. 15, 1983, p. 69 and following.
"A New Formula For Dairy Calf Rearing," Animal Nutrition & Health, Mar.; Apr., 1984, pp. 26, 28.

"Internal Parasites of Food Animals," Animal Nutrition & Health, Mar.–Apr., 1984, pp. 34, 43, 44.
An advertisement for Bluelite appearing in *Hog Farm Management*, Dec. 1983, p. 94.

*Primary Examiner*—Johnnie R. Brown
*Assistant Examiner*—Elli Peselev
*Attorney, Agent, or Firm*—Peterson, Wicks, Nemer & Kamrath

[57] ABSTRACT

Composition for treating dehydration in swine is described according to the preferred embodiment of the teachings of the present invention for adminstration in the drinking water or feed of pigs. Generally, the treatment composition is a palatable, electrolyte water-acidifier having mulitiple sources of energy that are readily consumable by most animals. Specifically, the composition includes citric acid which is very palatable and in a concentration to reduce the pH level of the water to which it is mixed in the range of at least 2.0 units. This reduction in pH helps restore the pH of the digestive tract to normal levels. The composition further includes saccharine in its most preferred form to increase palatability factors. Additionally, multiple energy sources are provided in the composition for a wide spectrum and prolonged energy reservoir and for increased palatabiltiy. Likewise, multiple sources of electrolytes are provided in the composition to increase palatability while insuring solubility without irritating the digestive tract.

18 Claims, No Drawings

COMPOSITION FOR TREATING DEHYDRATION

BACKGROUND

The present invention generally relates to treatment compositions and more specifically to compositions for treating dehydration in mammals.

Water represents over 50 percent of the body weight of mature mammals such as swine, calves, and other species. Since fat is almost free of water, young animals have a much higher percentage of water in their bodies than mature animals. For example, water represents almost 75 percent of a young piglet's body weight.

Electrolytes serve as the primary way in which the body balances its fluids in the three compartments of the body where the fluid is held. Through the electrolytes and their osmotic pressure, the body fluids are maintained at proper levels or balance between intracellular fluid in the cells in relation to the fluid of the interstitial tissue outside the cells and blood vascular fluid. Without adequate water and electrolytes, the body cannot maintain its proper fluid balance between the compartments and the tissues start to wither or dehydrate.

Dehydration of the cells and tissue lead to body shrink, reduced growth, and impaired maintenance and may result in death when the body loses between 7 to 15 percent of its normal body fluid. Young animals which have a very high percentage of their body weight in fluid are very subject to severe dehydration which contributes to high mortality.

Enteric and gastrointestinal disease caused by E. coli, TGE and Rotaviruses quickly dehydrate the body as the fluids and electrolytes are lost via the stools. This dehydration from diarrhea and scours may make the young animal subject to shock and death in a matter of a very short time or several hours.

It is well-established that enteric and gastrointestinal disease represent one of the single most important diseases affecting mammals today. The severity of these diseases is clearly demonstrated by the high losses which are sustained, not only by individual producers of domestic animals, but on a nationwide basis in terms of the overall agricultural economy as well. This means that there is a very significant reduction in the pounds of fresh meat, such as pork, beef or lamb which are available on the nation's market shelves in any given year.

Animals suffering from stress lose their body fluid reserves through respiration, via the kidneys and as a result of intestinal hypermotility that frequently manifests itself as scours or diarrhea. Changes in environment, weaning, long distance hauling, excessive handling, and disease are examples of stress that can result in extensive shrink or dehydration. In addition to short-term body weight loss, young animals may become stunted or have increased mortality if the shrink or dehydration is not corrected.

Thus, a need has arisen for a composition for treating dehydration.

It is therefore an object of the present invention to provide a novel composition for the treatment of dehydration.

It is further an object of the present invention to provide such a novel treatment composition for the treatment of enteric and gastrointestinal diseases.

It is further an object of the present invention to provide such a novel treatment composition of a relatively acidic nature which reduces the pH level in the digestive tract when ingested.

It is further an object of the present invention to provide such a novel treatment composition which maximizes energy and electrolyte absorption.

It is further an object of the present invention to provide such a novel treatment composition which can be conveniently added to drinking water and does not require intravenous or subcutaneous injection or other extraordinary, individual dosage administration.

It is further an object of the present invention to provide such a novel treatment composition which is extremely palatable for increasing the treatment composition and water intake.

It is further an object of the present invention to provide such a novel treatment composition which includes multiple sources of electrolytes.

It is further an object of the present invention to provide such a novel treatment composition which includes multiple sources of electrolytes for increasing palatability.

It is further an object of the present invention to provide such a novel treatment composition which includes multiple sources of saccharides providing a wider spectrum and prolonged energy reservoir.

It is further an object of the present invention to provide such a novel treatment composition which includes multiple sources of saccharides for increasing palatability.

It is further an object of the present invention to provide such a novel treatment composition which is water soluble.

These and further objects and advantages of the present invention will become clearer in light of the following detailed description of an illustrative embodiment of this invention.

DESCRIPTION

A treatment for dehydration according to the teachings of the present invention includes a composition which may be administered in the drinking water or feed of the animal and is described specifically for the treatment of dehydration in swine. In the most preferred embodiment of the present invention, one pound of treatment composition for swine can be mixed with 64 gallons of drinking water or 6 pounds of treatment composition for swine can be mixed with each ton of complete swine feed. For purposes of calculation, it is assumed that pigs normally consume between 8–12 percent of their body weight in water, depending upon temperature, stress, and disease. Thus, water intake guidelines on a daily basis utilized would be for a 15–20 pound pig consuming approximately ¼ to ½ gallon of water, a 20–30 pound pig consuming approximately ½ to ¾ gallon of water, and a 30–60 pound pig consuming approximately ¾ to 1 gallon of water. It can be appreciated that the treatment composition may be varied according to the teachings of the present invention for the treatment of dehydration in cattle and other species by a person skilled in the art after the teachings of the present invention become known.

Proper pH in the digestive tract of mammals has become known to be important in the health and well-being of the animal. The stomachs of piglets and young calves are acid in nature. The lining of the stomach has a pH of 3 and the ingesta (food material) in the healthy stomach of a young animal will have a pH of 5 or less. In the small intestine, the pH may go as high as 6 to 6.5.

During vomiting and in many cases of diarrhea, the pH of the stomach and intestine increases due to the loss of acid. Specifically, if the pH of the contents of the digestive tract should rise from a normal pH in the range of 5 or less to a pH in the range of 7 or neutrality, activation of the pro-enzyme pepsinogen to pepsin may be prevented interfering with protein breakdown, digestion, and absorption. Further, the cells of the digestive tract may be damaged. Additionally, *E. coli* bacteria, which are a primary cause of enteric and gastrointestinal disease, are known to proliferate and grow in the digestive tract when the pH is in the range of 5 or more whereas the bacteria are inhibited in a pH in the range of 3.6 and below.

Young animals have a limited ability to secrete acid in their digestive tract and thus are especially prone to higher pH levels in their digestive tracts. Thus, acidifiers have been tested prior to the present invention to help the young animal maintain the pH level in the digestive tract in the range of 2-3 especially under stress and/or enteric and/or gastrointestinal disease conditions. However, prior acidifiers have proven to be undesireable due to their high cost and more importantly their low palatability.

The composition of the present invention includes citric acid in a concentration sufficient to reduce the pH of water with which it is mixed in the range of at least 2 to 3 units. For example, the treatment composition according to the preferred embodiment of the present invention for use in the treatment of swine has a concentration in the range of 20 to 33 percent of the total ingredients and particularly a concentration in the range of 24.8 percent. Thus, upon intake of the treatment composition of the present invention to the digestive tract of the animal, the pH of the contents of the digestive tract will be advantageously reduced for restoring the stomach and intestine and their contents to more desirable pH levels.

It should further be appreciated that citric acid is considerably more palatable than prior acidifiers such as lactic acid used in prior treatment compositions. Palatability is of the utmost importance since the treatment composition must be ingested in the desired quantities to insure proper end treatment results.

It can then be appreciated that citric acid in concentrations sufficient to reduce the pH of water with which it is mixed in the range of 2 to 3 units such as concentrations in the range of 24.8 percent of total ingredients for swine treatment composition is very unique to the present invention. Specifically, although present in prior treatment compositions, citric acid was provided in prior treatment compositions at very low levels, typically in the range of 0.1-0.5 percent, and for the major purpose of increasing palatability of the compositions. Prior treatment compositions did not recognize the desireability of reducing the pH level present in the digestive tract and/or the desireability of using citric acid as an acidifier for reducing pH levels in the digestive tract. The treatment composition of the present invention is a recognition of the advantages of the use of citric acid in concentrations considerably greater than heretofor utilized or taught in prior treatment concentrations.

The composition of the present invention further includes saccharine, such as sodium saccharine, to increase palatability factors and to reinforce the desirable taste of the present invention. The composition of the present invention includes sodium saccharine in a concentration in the range of 2 to 3 percent of the total ingredients and particularly in the range of 1.1 to 2.2 percent of the total ingredients. Prior treatment compositions did not include saccharine and thus did not recognize that its inclusion would improve voluntary composition intake by the animal guaranteeing the required treatment dosage due to the increased palatability and desireability to animals especially to swine. Thus, although saccharine is known as a sugar substitute in the feed industry, inclusion of saccharine is unique in the treatment composition of the present invention to increase palatability and desirability and is not present in prior treatment compositions.

The composition of the present invention further includes monosaccharides such as dextrose and fructose and disaccharides such as sucrose and lactose in a combined concentration in the range of 65 to 77 percent of the total ingredients. Their presence increases palatability and provides carbohydrates for energy utilization by the animal. In this connection, it should be pointed out that the monosaccharides (dextrose and fructose) are rapidly available for metabolic use by the animal, whereas the disaccharides (sucrose and lactose) will provide for energy release at an initially slower rate, but will be maintained for a sustained period of time.

It should then be appreciated that the saccharides of fructose and sucrose are included in the treatment composition which is soluble in water of the present invention in addition to the saccharides of dextrose and lactose which are known to be provided in prior treatment compositions which are soluble in water. This unique feature of the treatment composition of the present invention results in several advantages over prior treatment compositions. For example, the utilization of the four types of saccharides in the treatment composition of the present invention result in multiple energy sources which provide a wider spectrum and prolonged energy reservoir as compared to one or two energy sources utilized in prior treatment compositions. This multiple energy source of the treatment composition of the present invention is of great value in alleviating the hypoglycemia or reduced blood sugar that is a primary contributing factor to the high mortality rate of enteritis. Additionally, fructose and sucrose each have flavors which are unique to each other and to dextrose and lactose. The utilization of the four types of saccharides in the treatment composition of the present invention result in multiple flavor sources which provide a wider spectrum of tastes as compared to one or two saccharides utilized in prior treatment compositions. Thus, the palatability of the treatment composition of the present invention is increased over the palatability of prior treatment compositions.

The treatment composition of the present invention also provides electrolytes in concentrations in the range of 2 to 4 percent of the total composition. However, rather than including 1 to 3 electrolytes as in prior treatment compositions, the treatment composition of the present invention includes multiple sources of electrolytes and specifically includes seven electrolytes. Particularly, the treatment composition of the present invention includes the four essential cations: potassium, magnesium, sodium and calcium which are required by the fluids in the tissue and three anions in the form of bicarbonate, phosphate, and chloride. These electrolytes and sulfate are believed to be the eight most essential electrolytes to combat dehydration and may be lost or severely depleted as the result of diarrhea or scours in young animals. Sulfate is often found at high levels in water from many farm wells. High levels of sulfate frequently irritate the mucosa of the digestive tract to result in mild forms of irritation which can result in diarrhea and may produce a cathartic action. Thus, the treatment composition of the present invention does not include sulfate to avoid any potential compounding effects when mixed with water already having high levels of sulfate.

The multiple sources of electrolytes are a unique feature of the treatment composition of the present invention over prior treatment compositions including 1 to 3 electrolytes and results in several advantages. First, lower levels of salt (sodium chloride) are present in the treatment composition of the present invention than present in prior treatment compositions. Salt reduces palatability and thus the treatment composition of the present invention has greater palatability than prior treatment compositions. Additionally, the treatment composition of the present invention allows the electrolyte ions to be present at low, balanced levels with respect to each other so as not to provide an excess of any one ion at the expense of the other. An excessive amount of any one ion such as potassium may result in a bad taste which reduces palatability and may further result in undesireable physiological reactions in the animal.

Thus, the electrolytes at the level in the present invention do not interfere with palatability. As a result, water intake can be increased so as to combat dehydration. Electrolytes are important in treating dehydration, but more significant is the water intake in an oral formulation. Animals drinking ample amounts of water, as a result of the invention, can obtain electrolytes from their daily feed ration to rehydrate themselves with both water and electrolytes.

Likewise, an excessive amount of any one ion in a similar manner as set forth for sulfate may cause irritation. Thus, the treatment composition of the present invention is a less irritating compound as compared with prior treatment compositions. Additionally, some forms of the electrolytes of the treatment composition of the present invention are in gluconate and lactate forms which are less irritating than other electrolytes so as not to irritate the intestinal tract when used to treat dehydration associated with enteritis and also serve as a source of energy. Further, the treatment composition of the present invention is more soluble in water and remains in solution better than prior treatment compositions. Specifically, each of the seven electrolytes provided in the treatment composition of the present invention have independent solubility factors. Thus, the probability of any one electrolyte reaching a level which might be undesirable in regard to toxicity, palatability, and/or solubility is greatly reduced even with well water which may include high levels of electrolytes such as magnesium, sodium, calcium and/or sulfate as compared to prior treatment compositions.

Thus, these multiple sources of electrolytes of the treatment composition of the present invention help maintain the fluids in the blood vessels, tissues and cells of the body because they are readily absorbed from the intestinal tract. The treatment composition of the present invention was specifically designed to assure rapid absorption of the electrolytes.

It should be appreciated that the unique combination of citric acid, electrolytes, and carbohydrates in the concentrations of the present invention produce advantageous results. Specifically, due to the presence of citric acid, the pH level of the contents of the digestive tract are reduced, thus increasing protein breakdown, digestion, and absorption, increasing water absorption, and increasing electrolyte absorption. When the citric acid of the present invention is ingested, the carbohydrates and electrolytes are also ingested simultaneously with the citric acid in the treatment composition of the present invention and are insured to be available to the blood of the animal to provide the energy necessary for combatting sickness and for growth.

Likewise, the components of the treatment composition of the present invention allow packaging in a single container while maintaining a highly stable form even when exposed to large variations in humidity and temperature. Further, the treatment composition of the present invention is simply mixed with water in water containers, water proportioners, watering tanks, and the like and premixing of different packs of components is not required as in prior treatment compositions. Thus, the treatment composition of the present invention can be easily administered by relatively unskilled personnel and without requiring veterinary or medical personnel.

A further understanding of the invention can be had from the following examples of nonlimiting, field trials. For example, a field trial was conducted on 24 stunted pigs which had been scouring for 7 to 10 days. The 12 heaviest pigs were used as controls and the 12 lightest were given treatment composition according to the present invention. The field trial yielded the following results:

| | Control Pigs | Treated Pigs |
|---|---|---|
| Average weight at start of 5 day trial | 20.2 lbs. | 16.6 lbs. |
| Average weight at end of 5 day trial | 23.8 lbs. | 20.9 lbs. |
| Total average gain in 5 days | 3.6 lbs. | 4.3 lbs. |
| Average daily gain | 0.72 lbs. | 0.86 lbs. |

Pigs treated with the treatment composition of the present invention consumed 20 percent more water than the control pigs (0.76 gallons versus 0.61 gallons/day) and after 48 hours, pigs treated with the treatment composition of the present invention showed no signs of dehydration and scours. It can then be appreciated that the scours of the treated pigs were effectively cured by the treatment composition of the present invention and the disadvantages of dehydration were also overcome.

Furthermore, the treatment composition of the present invention may be utilized for preventing and/or correcting dehydration caused from stress such as from weaning, moving, or handling animals. Specifically, if the treatment composition of the present invention is fed to animals subjected to such stress, water intake is substantially increased and reduced dehydration occurs. For example, a field trial was conducted on 40 pigs to test the value of the present invention during the weaning of the pigs at 3 weeks of age. The results were as follows:

| | Control Pigs | Treated Pigs |
|---|---|---|
| Average weight at weaning (start of trial) | 14.8 lbs. | 11.4 lbs. |
| Average weight 7 days after weaning | 16.8 lbs. | 16.5 lbs. |

|  | Control Pigs | Treated Pigs |
|---|---|---|
| Total average gain in weight | 2.0 lbs. | 5.1 lbs. |
| Average daily gain | .29 lbs. | .72 lbs. |
| Total water intake for first 5 days after weaning | 18 gallons | 29 gallons |

Pigs treated with the treatment composition of the present invention drank well over 30 percent more water the first 5 days after weaning and also consumed significantly more feed. It can then be appreciated that substantially greater water intake occurred in pigs treated with the composition of the present invention than pigs which were not treated with the composition of the present invention. Thus, dehydration is prevented or lessened with the present invention due to increased water intake.

It should then be noted that many prior treatments of dehydration relied upon intensive use of antibacterial agents, amino acids such as glycine, and mineral salts, intravenous or subcutaneous injection of electrolytes, and the like. Contrary to prior treatments which attempt to merely combat enteric and gastrointestinal diseases, the treatment composition of the present invention returns the digestive tract to an environment which is hostile to the presence and multiplication of agents which cause the enteric and gastrointestinal diseases and which is in a pH range for proper, healthy, normal digestion. Further, in the pH range of the digestive tract created by the treatment composition of the present invention, absorption of energy and electrolytes by the digestive tract is enhanced and optimized for return to healthy condition and normal growth.

It should be appreciated that the treatment composition according to the teachings of the present invention is designed with considerable emphasis on palatability. Prior treatment compositions either did not pay or paid little attention to palatability. However, with the increased palatability and the acidic nature of the treatment composition of the present invention, water intake is significantly increased to help reduce shrink or dehydration. In fact, the treatment composition of the present invention may be used in conjunction with most medicants or drugs to cover the taste of unpalatable medicants or drugs used in treating infections due to its extremely palatable nature.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. Composition for treatment of enteric and gastrointestinal diseases, including dehydration, in mammals having digestive tracts, with the treatment composition being orally administered in the drinking water or feed of the mammal for introduction into the digestive tract comprising: an amount of citric acid effective to reduce the pH level of the contents of the digestive tract of the mammal for restoring the digestive tract to normal pH levels form pH levels of the digestive tract present during dehydration to increase water, protein, and electrolyte absorption by the digestive tract, with the citric acid being in the range of 20 to 33 percent of the total ingredients and sufficient to reduce the pH of the daily water intake of the mammal in the range of at least 2 to 3 units; and an amount of four types of saccharides selected from monosaccharides and disaccharides effective as a source of energy for metabolic use by the mammal to provide a wide spectrum and prolonged energy reservoir and to provide a wide spectrum of tastes for further enhancing the palatability of the treatment composition to increase treatment composition intake, wherein the monosaccharides are dextrose and fructose and with the disaccharides being sucrose and lactose.

2. The treatment composition of claim 1 for treatment of swine.

3. The treatment composition of claim 2 wherein the citric acid is in a concentration in the range of 24.8 percent of the total ingredients.

4. The treatment composition of claim 1 wherein the saccharides are provided in a concentration in the range of 65 to 77 percent of the total ingredients.

5. The treatment composition of claim 4 further comprising: an amount of saccharine effective to further increase palatability factors of the treatment composition and to reinforce the desireable taste of the treatment composition.

6. The treatment composition of claim 5 wherein the saccharine is provided in a concentration in the range of 2 to 3 percent of the total ingredients.

7. The treatment composition of claim 6 wherein the saccharine comprises: sodium saccharine.

8. The treatment composition of claim 4 further comprising: multiple sources of electrolytes, with each source of electrolyte having relatively low levels to increase palatability, to reduce the possibility of irritation to the digestive tract, and to increase solubility of the treatment composition.

9. The treatment composition of claim 8 wherein the multiple sources of electrolytes are in a concentration in the range of 2 to 4 percent of the total ingredients.

10. The treatment composition of claim 8 wherein the multiple sources of electrolytes comprise: potassium, magnesium, sodium, calcium, bicarbonate, phosphate, and chloride.

11. Composition for treatment of enteric and gastrointestinal diseases in mammals having digestive tracts, with the treatment composition being orally administered in the drinking water or feed of the mammal for introduction into the digestive tract comprising: an amount of effective agent for combatting said disease of the mammal; an amount of four types of saccharides selected from monosaccharides and disaccharides effective as a source of energy for metabolic use by the mammal to provide a wide spectrum and prolonged energy reservoir and to provide a wide spectrum of tastes for further enhancing the palatability of the treatment composition to increase treatment composition intake, wherein the monosaccharides are dextrose and fructose and with the disaccharides being sucrose and lactose; an amount of saccharine effective to increase palatability factors of the treatment composition and to reinforce the desirable taste of the treatment composition, with the treatment composition being administered for the treatment of dehydration in mammals and with the combatting agent comprising: an amount of citric acid effective to reduce the pH level of the contents of the digestive tract of the mammal for restoring the digestive tract to normal pH levels from pH levels of the digestive tract present during dehydration to increase water, protein, and electrolyte absorption by the digestive tract, with the amount of citric acid being sufficient to reduce the pH level of the daily water intake of the mammal in the range of at least 2 to 3 units.

12. The treatment composition of claim 11 wherein the saccharides are provided in a concentration in the range of 65 to 77 percent of the total ingredients.

13. The treatment composition of claim 12 wherein the saccharine is provided in a concentration in the range of 2 to 3 percent of the total ingredients.

14. The treatment composition of claim 13 wherein the saccharine comprises: sodium saccharine.

15. The treatment composition of claim 12 further comprising: multiple sources of electrolytes, with each source of electrolyte having relatively low levels to increase palatability, to reduce the possibility of irritation to the digestive tract, and to increase solubility of the treatment composition.

16. The treatment composition of claim 15 wherein the multiple sources of electrolytes comprise: potassium, magnesium, sodium, calcium, bicarbonate, phosphate, and chloride.

17. The treatment composition of claim 12 for treatment of dehydration of swine, and wherein the citric acid is in a concentration in the range of 20 to 33 percent of the total ingredients.

18. The treatment composition of claim 17 wherein the citric acid is in a concentration in the range of 24.8 percent of the total ingredients.

* * * * *